US008101200B2

(12) United States Patent
Whitbourne et al.

(10) Patent No.: US 8,101,200 B2
(45) Date of Patent: Jan. 24, 2012

(54) TARGETED THERAPEUTIC AGENT RELEASE DEVICES AND METHODS OF MAKING AND USING THE SAME

(75) Inventors: Richard J. Whitbourne, Rochester, NY (US); Daniel Hullihen, Avon, NY (US); Michael R. Violante, Pittsford, NY (US); Frank Guo-Bin Wang, New Haven, CT (US); Xianping Zhang, Webster, NY (US)

(73) Assignee: Angiotech BioCoatings, Inc.

( * ) Notice: Subject to any disclaimer, the term of this patent is extended or adjusted under 35 U.S.C. 154(b) by 344 days.

(21) Appl. No.: 09/834,307

(22) Filed: Apr. 12, 2001

(65) Prior Publication Data

US 2002/0018795 A1 Feb. 14, 2002

Related U.S. Application Data

(60) Provisional application No. 60/196,781, filed on Apr. 13, 2000.

(51) Int. Cl.
*A61F 2/00* (2006.01)
(52) U.S. Cl. .......... 424/426; 424/422; 424/423; 424/424
(58) Field of Classification Search .................. 424/423, 424/457, 458, 78.24, 78.27, 461, 462, 463, 424/468, 409, 494, 497, 422, 484, 487, 488; 514/772.1, 772.2, 772.3, 777; 604/187, 313, 604/318
See application file for complete search history.

(56) References Cited

U.S. PATENT DOCUMENTS

| 4,531,933 A | | 7/1985 | Norton et al. | |
| 4,723,957 A | | 2/1988 | Magruder et al. | ............... 424/78 |
| 5,001,009 A | | 3/1991 | Whitbourne | ................ 428/412 |
| 5,059,211 A | | 10/1991 | Stack et al. | |
| 5,069,899 A | * | 12/1991 | Whitbourne | ................... 424/56 |
| 5,294,448 A | | 3/1994 | Ring et al. | .................... 424/497 |
| 5,306,286 A | | 4/1994 | Stack et al. | |
| 5,331,027 A | | 7/1994 | Whitbourne | ................... 524/37 |
| 5,523,092 A | | 6/1996 | Hanson et al. | |
| 5,525,348 A | * | 6/1996 | Whitbourne et al. | ........ 424/423 |
| 5,589,120 A | * | 12/1996 | Khan et al. | .................... 264/130 |
| 5,616,608 A | | 4/1997 | Kinsella et al. | |
| 5,660,829 A | | 8/1997 | Burke et al. | ............... 424/178.1 |
| 5,707,385 A | | 1/1998 | Williams | |
| 5,716,981 A | | 2/1998 | Hunter et al. | |
| 5,733,925 A | | 3/1998 | Kunz et al. | |
| 5,779,673 A | | 7/1998 | Roth et al. | .................... 604/101 |
| 5,797,898 A | | 8/1998 | Santini, Jr. et al. | |
| 5,800,412 A | | 9/1998 | Zhang et al. | .................. 604/280 |
| 5,840,329 A | | 11/1998 | Bai | .............................. 424/458 |
| 5,843,172 A | | 12/1998 | Yan | |
| 5,866,619 A | | 2/1999 | Sintov et al. | ................... 514/777 |
| 5,882,335 A | | 3/1999 | Leone et al. | |
| 5,972,027 A | | 10/1999 | Johnson | |
| 5,977,163 A | | 11/1999 | Li et al. | ......................... 514/449 |
| 5,977,315 A | | 11/1999 | Chatterjee et al. | ............ 530/387 |
| 5,980,550 A | * | 11/1999 | Eder et al. | ..................... 606/191 |
| 5,994,309 A | | 11/1999 | Mazar et al. | ..................... 514/16 |
| 5,997,517 A | * | 12/1999 | Whitbourne | ................... 604/265 |
| 6,001,386 A | | 12/1999 | Ashton et al. | ................. 424/423 |
| 6,071,305 A | | 6/2000 | Brown et al. | |
| 6,074,659 A | | 6/2000 | Kunz et al. | |
| 6,096,070 A | | 8/2000 | Ragheb et al. | |
| 6,110,483 A | * | 8/2000 | Whitbourne et al. | ......... 424/423 |
| 6,171,609 B1 | | 1/2001 | Kunz | |
| 6,231,888 B1 | | 5/2001 | Lerner et al. | ................... 424/463 |
| 6,241,762 B1 | | 6/2001 | Shanley | |
| 6,254,632 B1 | | 7/2001 | Wu et al. | |
| 6,268,390 B1 | | 7/2001 | Kunz | |
| 6,273,908 B1 | | 8/2001 | Ndondo-Lay | |
| 6,273,913 B1 | | 8/2001 | Wright et al. | |
| 6,293,967 B1 | | 9/2001 | Shanley | |
| 6,306,176 B1 | * | 10/2001 | Whitbourne | ............... 623/23.59 |
| 6,306,421 B1 | | 10/2001 | Kunz et al. | |
| 6,335,029 B1 | * | 1/2002 | Kamath et al. | ................ 424/423 |
| 6,395,326 B1 | | 5/2002 | Castro et al. | |
| 6,403,635 B1 | | 6/2002 | Kinsella et al. | |

(Continued)

FOREIGN PATENT DOCUMENTS

EP 0850604 7/1998

(Continued)

OTHER PUBLICATIONS

S. Cakmakli et al, abstract of article "A Prospective Evaluation of the Treatment of Primary or Metastatic Liver Carcinoma With Hepatic Arterial Infusion Chemotherapy", Acta Oncol, 1996, 35(4):441-4.

(Continued)

*Primary Examiner* — Michael G Hartley
*Assistant Examiner* — Micah-Paul Young

(57) ABSTRACT

Generally, the present invention provides devices and methods for delivering high, efficacious concentrations of therapeutic agents, i.e., medicaments such as drugs, antibiotics, etc., to specific sites in a patient's body, such as tumors and infected lesions. In one aspect of the present invention there are provided devices to accomplish the aforesaid delivery of therapeutic agents and methods to accomplish the delivery by positioning a device in the body using minimally invasive techniques such as, for example, catheterization or via trochar. The devices may contain a carrier substrate and a coating on the substrate. The carrier substrate provides structural integrity to the device and the coating thereon contains at least one layer of polymeric material containing one or more medicaments. Optionally, there may be a non-medicated binder coat between the carrier substrate and the medicated polymer layer. The medicated polymer layer may contain a hydrophilic/hydrophobic polymer composition.

60 Claims, 1 Drawing Sheet

U.S. PATENT DOCUMENTS

| | | |
|---|---|---|
| 6,491,666 B1 | 12/2002 | Santini, Jr. et al. |
| 6,491,938 B2 | 12/2002 | Kunz et al. |
| 6,515,009 B1 | 2/2003 | Kunz et al. |
| 6,515,016 B2 | 2/2003 | Hunter |
| 6,562,065 B1 | 5/2003 | Shanley |
| 6,599,928 B2 | 7/2003 | Kunz et al. |
| 6,616,765 B1 | 9/2003 | Castro et al. |
| 6,656,162 B2 | 12/2003 | Santini, Jr. et al. |
| 6,663,662 B2 | 12/2003 | Pacetti et al. |
| 6,699,281 B2 | 3/2004 | Vallana et al. |
| 6,783,543 B2 | 8/2004 | Jang |
| 7,041,130 B2 | 5/2006 | Santini, Jr. et al. |
| 7,052,488 B2 | 5/2006 | Uhland |
| 7,135,039 B2 | 11/2006 | De Scheerder et al. |
| 2001/0032011 A1 | 10/2001 | Stanford |
| 2002/0038145 A1 | 3/2002 | Jang |
| 2002/0082680 A1 | 6/2002 | Shanley et al. |
| 2004/0166140 A1 | 8/2004 | Santini, Jr. et al. |
| 2005/0181977 A1 | 8/2005 | Hunter et al. |
| 2005/0283228 A1 | 12/2005 | Stanford |
| 2006/0129231 A1 | 6/2006 | De Scheerder et al. |

FOREIGN PATENT DOCUMENTS

| | | |
|---|---|---|
| EP | 0950386 | 10/1999 |
| EP | 1261297 | 12/2002 |
| WO | WO 98/19713 | 5/1998 |
| WO | WO 98/23228 | 6/1998 |

OTHER PUBLICATIONS

N. Kemeny et al, abstract of article "Hepatic Arterial Infusion of Chemotherapy After Resection of Hepatic Metastases From Colorectal Cancer", The New England Journal of Medicine, Dec. 30, 1999, vol. 341, No. 27, pp. 2039-2048.

T. Kato et al, abstract of article "Targeted Cancer Chemotherapy With Arterial Microcapsule Chemoembolization: Review of 1013 Patients", Cancer Chemother Pharmacol, 1996; 37(4):289-96.

K. Sato et al, abstract of article "Arterial Chemoembolization Using Microencapsulated Anticancer Drugs", Gan to Kagaku Ryoho, Jun. 1990, 17(6):1105-10.

* cited by examiner

TARGETED THERAPEUTIC AGENT RELEASE DEVICES AND METHODS OF MAKING AND USING THE SAME

CROSS-REFERENCE TO RELATED APPLICATION

This application claims benefit of U.S. provisional application No. 60/196,781 filed Apr. 13, 2000.

BACKGROUND OF THE INVENTION

1. Field of the Invention

The present invention is concerned with implantable devices having a polymer layer containing one or more therapeutic agents, i.e., a medicament or medicaments, which devices are implantable into specific sites, such as tumors or lesions, in a patient's body for sustained time-release of the one or more medicaments into the specific site, and to methods of making and using such implantable devices.

2. Related Art

Modern solid tumor cancer therapy typically proceeds along multiple fronts. Surgical resection, radiotherapy, and chemotherapy are the most common treatment modes, and they are ordinarily used in various combinations. For instance, resection procedures are usually followed by radiotherapy and/or chemotherapy in an attempt to eliminate metastatic cells which have traveled from the tumors. These treatments are usually traumatic for patients, and often fail to eliminate the disease.

Surgical resection involves the removal of neoplastic tissue along with contiguous tissue, which may contain some tissue that was inadvertently released from the tumor during the resection procedure. For this reason, resection is usually followed by radiotherapy and/or chemotherapy. The procedure is traumatic, and leads to physical and esthetic deformation. The procedure exposes patients to high risks of hospital-acquired nosocomial infections which may be difficult to treat because drug resistant organisms (Super Bugs) are often involved, and the patients are often immunocompromised because of disease.

Radiotherapy involves exposure of neoplastic tissue to radiation designed to kill the cancerous tissue. The technology has advanced to the point where multiple doses can be simultaneously focused on the lesion. This provides higher dosing in the lesion while surrounding tissue is exposed to lower doses of radiation. This technology involves complex algorithms, and dosing errors of an order of magnitude or greater can result. Also, significant collateral damage is inflicted on surrounding tissue.

Brachytherapy uses radioactive "seeds" which must be placed correctly in the tumor or correspondingly inappropriate dosing occurs. The method is very skill-dependent in order to achieve successful outcomes. Brachytherapy has not developed a long record of clinical utility.

Chemotherapy involves the administration of cytotoxic agents to patients. These agents are used because they exhibit selective cytotoxicity, and their action against neoplastic tissue can be up to several times that against normal tissue. Chemotherapy is ordinarily administered systemically, usually in aliquots over periods of several days or weeks. This is done in order to reduce unintended adverse effects that result from systemic drug concentrations which are too high to be tolerated by patients. This method is compromised by the fact that maximum systemic drug doses tolerated by patients produce drug concentrations in tumors that are well below the ideal concentrations required to achieve maximum efficacy. Considerable collateral tissue damage results because of the relatively high systemic drug concentrations that are required to achieve significant anti-tumor activity. Patients may become susceptible to infection because drug infusion and disease can compromise their immune systems.

A major problem with chemotherapy as currently practiced is that much of the drug does not reach the intended target tissue. Systemic drug delivery results in administration of drug to a general compartment (e.g., vasculature) for distribution throughout the body. Some of the drug does reach the intended target site, but most is distributed elsewhere. This "non-targeted" drug is responsible for the adverse effects associated with chemotherapy. Ultimately, of course, the drug is metabolized and excreted from the body.

In contrast, targeted drug delivery provides for the bulk of the drug to be administered directly to the desired site. Some drug still reaches the central compartment for general distribution to non-target tissues, but most of the drug is available for therapeutic effect and only a small fraction results in adverse effects.

Various forms of targeted drug delivery have been investigated in an effort to enhance chemotherapy by increasing drug concentrations in the tumors while reducing the systemic drug concentrations. Targeted chemotherapy has been delivered via catheters into vessels feeding tumors or organs containing tumors. In most cases, the medicament or medicaments wash through the tumor too quickly and thus fail to maintain the sustained high, efficacious in-tumor drug concentrations needed for more effective therapy. The results have been somewhat better than systemic administration of chemotherapy, but not as good as desired. Various other techniques employ systemic administration of one or more medicaments that are intended to selectively absorb onto or into tumors, but these techniques result in undesirably high systemic drug levels.

Whitbourne U.S. Pat. No. 5,997,517 discloses bond coats for binding polymeric compositions ("top coats") onto various devices. Several examples show top coats comprising polyvinyl pyrrolidone (PVP) and nitrocellulose.

Whitbourne et al U.S. Pat. No. 5,069,899 discloses coatings for medical devices that can contain anti-thrombogenic and anti-microbial compositions. One disclosed coating containing a heparin compound comprised PVP and nitrocellulose (Example 1).

Whitbourne et al U.S. Pat. No. 5,525,348 discloses coating compositions containing anti-thrombogenic and/or anti-microbial agents. The coating contains water-insoluble polymers that may range from hydrophilic to hydrophobic.

Li et al U.S. Pat. No. 5,977,163 discloses a targeted drug delivery technique that involves linking paclitaxel or docetaxel to water soluble chelators, polyethylene glycol or a biodegradable polymer such as polyglutamate (PG-TXL). This linkage makes the paclitaxel or docetaxel water soluble, and causes it to selectively absorb into tumors. For example, animal testing showed that more than 300% of the equivalent maximum human dose of paclitaxel can be achieved. However, this method still involves substantial systemic drug concentrations with all of the potential side affects associated with such dosing levels. The use of water-soluble paclitaxel as a coating on implanted medical devices for the inhibition of restenosis is also discussed (col. 5, line 66-col. 6, line 43; col. 9, lines 23-43).

K. Sato et al (Gan To Kagaku Ryoho 1990, Jun. 17(6): 1105-10) discloses selective intraarterial infusion of ethylcellulose microcapsules containing an anticancer drug which exerts its therapeutic affects through infarction and sustained drug action (i.e., chemoembolization). This technique relies on the microcapsules embolizing the tumor vasculature and the subsequent diffusion of one or more drugs throughout the tumor(s). The results were better for bladder cancer (54% substantial tumor reduction (STR)), and prostate carcinoma (54% STR), but results were much lower for renal cell carcinoma and hepatoma.

Kato et al (Cancer Chemother Pharmacol 1996; 37(4):289-96) reviewed the feasibility of intra-arterial infusion of microencapsulated anticancer drugs (chemoembolization). Ethylcellulose microcapsules containing mitomycin C (median total dose 20 mg), cisplatin (60 mg) or peplomycin (40 mg) were given to tumor-feeding arteries by bolus injection. Mitomycin C microcapsules produced a higher response rate. Complete or partial remission of intractable pain and genitourinary gross hemorrhage was found in two-thirds of eligible patients. This modality is promising, but suffers from the inability to target individual tumors, thus patients experience adverse affects, and drug concentrations in the tumors is less than desired relative to the background liver tissue.

Kemeny et al (New England Journal of Medicine 1999; 341:2039-48) treated patients with six cycles of hepatic arterial infusion with floxuridine and dexamethazone plus intravenous fluorouracil, with or without leucovorin. The study showed improvement in survival, but involved systemic infusions of cytotoxic agents and adverse affects were seen in patients.

Caklakli et al (Acta Oncol 1996; 35(4):441-4) evaluated the efficacy of hepatic arterial infusion chemotherapy in the treatment of primary or metastatic liver carcinoma in 37 patients. The infusions were administered through a catheter that was placed in the hepatic artery, either surgically or by percutaneous puncture of the femoral artery. A complete response was observed in four patients. A partial response was observed in six patients and a minor response in another six. In nine patients the disease stabilized, while progression of the disease developed in 12 patients. The response rate (complete, partial, and minor responses) was 43.2% and median survival was 12.0 months. These results are promising. However, there were 17 Grade III toxicities observed, and the therapy was not directed primarily or directly into the patients' tumor or tumors.

The delivery of one or more medicaments to specific sites in a patient's body is an issue in fields other than the treatment of tumors. For example, in clinical practice, new strains of organisms have emerged which exhibit significantly more resistance to antibiotic therapy than do previously known strains. Antibiotics are normally administered systemically, either orally or via intravenous injection, so that systemic concentrations which are safe for most patients are achieved. However, these concentrations are below effective levels in the cases of some of the emerging drug-resistant organism strains. It would be advantageous in many cases if one or more medicaments providing anti-infective therapy could be targeted to infected lesions or other specific sites. In this way, it would be possible to achieve higher, more efficacious drug concentrations in the lesions, while systemic drug concentrations would remain at or below levels which are safe for most patients. As with cancer site-targeted therapy, site-targeted antibiotic therapy would be expected to be significantly more efficacious than systemic treatment.

It will be seen from the foregoing that need exists for achieving efficacious drug or other medicament concentrations in tumors for extended time periods without concurrent high systemic drug concentrations and for targeted delivery of anti-infective agents such as antibiotics, to sites such as infected lesions.

SUMMARY OF THE INVENTION

The present invention provides a medicated device comprising a scaffold member suitable for implantation at a tumor or other lesion site, a polymeric coating ("med coat") on the scaffold member, and at least one therapeutic agent in the med coat at a loading sufficient to provide therapeutic quantities of the therapeutic agent to the site for an extended period of time.

According to one aspect of the invention, the device may comprise an anti-cancer therapeutic agent in the med coat. Optionally, there may be at least 5 micrograms (μg) of at least one therapeutic agent per square centimeter of the med coat or, optionally, at least 50 μg of at least one therapeutic agent per square centimeter of the med coat or, optionally, at least 100 μg of at least one therapeutic agent per square centimeter of the med coat or, optionally, at least 500 μg of at least one therapeutic agent per square centimeter of the med coat.

According to another aspect of this invention, the device may comprise sufficient quantity of a therapeutic agent to deliver a therapeutically effective quantity of a therapeutic agent into tissue in a region of at least one centimeter from the device or, optionally, in a region of at least two centimeters from the device.

According to still another aspect of this invention, the med coat may comprise a hybrid polymer coating comprising a hydrophilic polymer component and a hydrophobic polymer component. In one particular embodiment, the polymer coating may comprise an acrylate polymer and PVP/VA copolymer in a weight ratio in the range of from 1.5:1 to 7:1.

This invention also provides a medicated device comprising a substrate suitable for implantation in a patient's body a polymeric coating ("med coat") on the scaffold member, and at least one therapeutic agent in the med coat at a loading sufficient to provide therapeutic quantities of the therapeutic agent to the patient's tissue in a region in the body extending at least one centimeter, optionally at least two centimeters, from the device.

In one preferred embodiment, the device may comprise a hybrid polymer coating comprising a major proportion of one or more hydrophilic polymer materials and a minor proportion of nitrocellulose, e.g., about 3% by weight of the combined weights of cellulose ester polymer such as nitrocellulose and the hydrophobic materials. In another preferred embodiment, the device may comprise a hybrid polymer coating comprising major portions of hydrophobic and hydrophilic polyurethanes, and cellulose ester such as nitrocellulose, and may contain minor portions of PVP and/or PVP/VA.

DETAILED DESCRIPTION OF THE INVENTION

Figure 1:
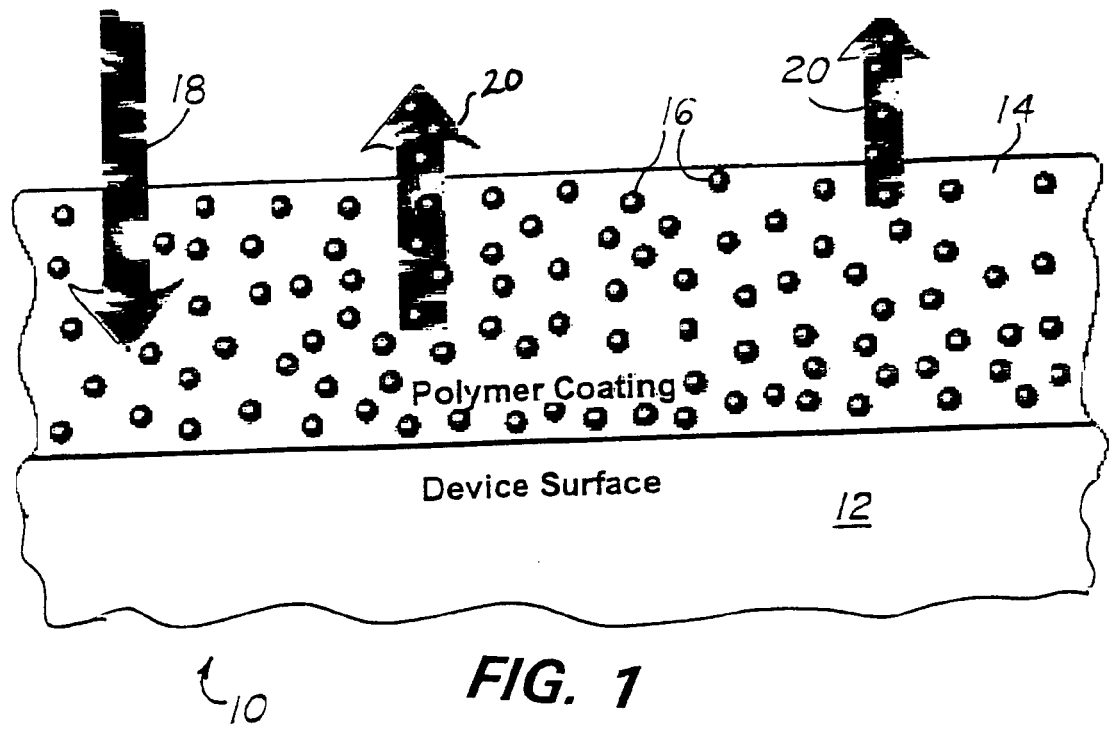
FIG. 1 is a schematic cross section of a device in accordance with one embodiment of the present invention.

The devices of the present invention can be inserted into lesion/malignant tissue, parenchyma or into the tumor/lesion vasculature where they serve to release therapeutic quantities of a therapeutic agent thereto. The devices comprise substrates that bear one or more layers of medicament-containing polymeric material, or "medicated polymer layers" or "med coats", from which at least one medicament diffuses out into the surrounding medium when hydrated. Body fluid is typically taken up in the medicated polymer layer of the device, and the one or more therapeutic agents, sometimes herein referred to as medicaments or drugs, are released into the surrounding tissue via the fluid. Generally, the present invention provides devices and methods for delivering high, efficacious concentrations of therapeutic agents, i.e., medicaments such as drugs, antibiotics, etc., to specific sites in a patient's body, such as tumors and infected lesions. In one aspect of the present invention there are provided devices to accomplish the aforesaid delivery of therapeutic agents and methods to accomplish the delivery by minimally invasive techniques such as, for example, catheterization or via a trochar.

A particular advantage of this aspect of the invention is that the medicated polymer layer does not need to have high mechanical strength since it relies on the substrate for physical integrity. Prior art implantable products for the delivery of therapeutic agents comprise drug-impregnated polymeric beads or sponges or biodegradable polymers and the like which rely on the physical properties of the impregnated polymer for their physical integrity. Materials commonly used for this purpose in prior art devices include polymethylmethocrylate, ethyl cellulose, poly(L-lactic acid) and/or blends of poly(L-lactic acid) with polycaprolactone or other bioerodable. However, the present invention provides a substrate on which the drug-containing coating layer is carried so the choices of polymers that may be used in the coating formulations of the present invention are far broader than with the other technologies. The present invention provides polymeric matrices that can match the needs for each product mission in terms of drug release rates, drug stabilization, drug compatibility, resistance to degradation caused during sterilization, and in vivo exposure. Conversely, the choice of materials used for the carrier substrate is not restricted to those capable of releasing therapeutic agents.

In another aspect of the present invention, the devices are of such size and shape as to allow them to be delivered to a target site, such as a tumor or lesion, for example, by a trochar or catheter placement or otherwise. Such devices may be shaped as mandrels, beads, cylinders, egg-shaped articles, spheres, coiled or straight articles such as threads or wires, or other configurations. Such articles may have dimensions ranging from diameters of less than 1 mm to greater than 10 mm, and lengths of up to 40 centimeters ("cm") or more. Typically, the largest dimension (length, width or height) for an implantable device is not more than 10 mm, e.g., in the range of from 2 to 5 mm. Such shapes and dimensions are merely illustrative of some embodiments of the invention, and are not intended to limit the dimensions or shapes of the articles that are embraced by the invention. In certain embodiments, the substrate on which one or more polymer coatings are applied is configured to serve as a scaffold for the coating materials. A "scaffold" is a substrate configured to have adjacent edges or surfaces in close proximity to each other so that the coating material, when applied, will not only coat the surfaces but will bridge from one surface to the other. For example, a scaffold may be provided by a wire configured into a coil having open windings. When the polymer coating is applied to the scaffold, it not only covers the surface of the wire but also bridges from one winding to the next so that the finished device may have the shape of a cylinder with the coiled wire scaffold embedded therein. Other scaffolds include perforated wafers, wire meshes, and the like. Thus, a scaffold differs from other substrates such as straight wires, pellets, tubing, stents and other devices to which lubricious coatings have been applied in the prior art. In all such embodiments, the scaffold provides the structural support for the device so that the coating material can be chosen for its rate of release of the drugs incorporated therein without regard to the structural strength of the coating itself.

Depending on which substrate material is selected, the coating containing the medicated polymer layer (the "med coat") may comprise one or more layers. The medicated polymer layers of this invention may be applied directly on substrates such as polyvinylchloride (PVC) and many polyurethanes. Other substrates exhibit better adhesion when one or more layers of bonding material are used in order to prime the surface so that the medicated layer(s) will be properly anchored to the substrate. Metals such as stainless steel, and some plastics such as polyamides or polyolefins can require such priming layers to achieve the adherence needed on medical devices intended for in vivo placement. Such bonding layers are described in U.S. Pat. No. 5,997,517 and its divisional applications and continuation-in-part applications, and foreign counterparts thereof, the respective disclosures of which are incorporated herein by reference.

Briefly restated, U.S. Pat. No. 5,997,517 teaches that thin bond or tie coat layers may be applied to difficult-to-bond-to substrates in order that other layers which cannot normally be bonded to such substrates may be satisfactorily bonded. The polymers used for this purpose are sufficiently resistant to degradation by solvents in succeeding layers that the coating does not lose adhesiveness when soaked in water and is impervious to water diffusion from the surface. Classes of polymers which may be employed include acrylic polymers and copolymers based on monomers such as methylmethacrylate, butylmethacrylate, isobutylmethacrylate, ethyl methacrylate, methylacrylate, acrylic acid, styrene methacrylate, styrene acrylate, and others; vinyl polymers and copolymers such as polyvinylpyrrolidone, vinylpyrrolidone-vinylacetate copolymers, ethylene acrylic acid copolymers, epoxy polymers, and others. Exemplary commercial products that may be used in the invention include acrylics such as ARYLOID® (Rohm & Haas) AT-63, AT-51, AT-81, WR-97; Polyvinylpyrrolidone polyvinyl acetate copolymers such as PVP/VA (GAF) E-335, E-635; ethylene acrylic acid copolymers such as PRIMACOR™ (DOW) 5989, 5990; melamine resins such as CYMEL (CYTEC Industries) 303, 370, 380; epoxies such as EPON (Shell) 1001. Other appropriate polymers having the requisite characteristics will be apparent to persons of ordinary skill in the art.

The bonding polymers preferably, but not necessarily, contain reactive groups or points of reactivity such as hydroxyls, mono-, di- and tertiary amines, acids such as carboxyl, amides, or other groups which represent points of chemical reactivity. The bonding polymers and points of chemical reactivity are able to form attractive forces such as hydrogen bonding toward the medical device surface, and also toward the coating layers to be applied over them. Such bonds are very strong, and prevent penetration of the top coat layer and water without requiring covalent or other ionic links between the device surfaces and the thin polymer tie coatings.

Polymers with reactive groups are preferred to help bond with substrates like metals. However, bonding polymers lacking such groups such as acrylic or styrene polymers may also be used.

The reactive groups can also react to form a cross-linked matrix or help to form a cross-linked matrix. If desired, cross-linkers such as urea resins, melamines, isocyanates, phenolics, and others may be incorporated to cross-link the polymers of the invention with themselves, by reacting with the points of chemical reactivity on the polymer chains. Alternatively, cross-linkers may react with themselves to form a cross-linked matrix in which the tie coat polymers are enmeshed, resulting in a solvent-resistant layer. Cross-linking within the thin polymeric tie coats (either between the principal polymers or around them) is useful in promoting effective adhesion by ensuring that the solvents used in succeeding coating layers do not attack and degrade the tie coat polymer layer excessively and by resisting water penetration. When the tie coat layers are subjected to excessive solvent attack the tie coat polymer layer may be diluted by the succeeding coating layer thereby degrading the adhesive bond between the tie coat layer and the medical device surface. Excessive water penetration can also degrade adhesion.

Bond coatings according to the invention may be prepared with polymers that lack points of reactivity, such as acrylic or styrene polymers or copolymers. Likewise, coatings may be made without cross-linking. However, with such coatings a greater tie coat thickness may be required or desirable than with layers made of polymers with points of reactivity and layers with cross-linking, in order to achieve a high degree of adhesion of succeeding layers according to the invention.

The bond coat or layer may be thin, on the order of 0.0002 inch to 0.0005 inch (5 to 12 micrometers or "microns"), although it may be as thick as is desirable. Preferably, it is in the range of about 2 to about 100 microns, more preferably less than about 80 microns, or 60 microns, and particularly preferred embodiments are less than about 15 microns thick. Bond coats of about 2 to about 10 microns are generally quite adequate. If the coating is thicker, it may cause other problems in certain applications where thinness is important.

Examples of substrates and bond coat formulations that are effective with them are listed below. Many other combinations will be apparent to a person of ordinary skill in the art following the teachings of the invention.

stainless steel substrate:
  epoxy resin; vinylpyrrolidone-vinyl acetate copolymer; styrene acrylic aqueous dispersion; ethylene acrylic acid copolymer plus melamine resin; ethylene acrylic acid copolymer plus melamine resin plus hydroxyl function acrylic polymer plus isocyanate polymer; carboxyl function acrylic polymer plus epoxy resin; acrylic dispersion polymer
polyethylene substrate:
  ethylene acrylic acid copolymer plus melamine resin plus hydroxyl function acrylic polymer plus isocyanate polymer ethylene acrylic acid copolymer plus melamine resin plus hydroxyl function acrylic polymer plus isocyanate polymer plus oxygen plasma
polyester substrate:
  ethylene acrylic acid copolymer plus melamine resin plus hydroxyl function acrylic polymer plus isocyanate polymer
polyamide substrate:
  oxygen plasma plus polyvinylbutynal The bond coatings may be coherent in that they form a continuous surface layer. When coated with a top coat such as a medicated polymer layer, the resulting coatings are resistant to removal on prolonged soaking in aqueous fluids, and are adherent to a wide variety of substrates.

The bond coatings may be applied by various techniques such as dip, spray, brush, wipe, or other methods known to those skilled in the art. The coating solutions have low viscosities, typically less than 100 CPS, and have good spreading properties. The coatings are baked at elevated temperatures, typically 50° C. to 100° C., to drive off the organic solvents.

Gas plasma treatment may be done according to conventional methods. A vacuum is drawn, a gas such as oxygen or ammonia is allowed in, it is excited with Rf radiation, and the surface is allowed to stay in contact with the resulting plasma for a sufficient time, such as 20 minutes, to put functional groups on the surface. Oxygen produces hydroxyl surface groups, and ammonia produces amine groups covalently bound to the polymer surface. Over time the groups tend to fold into the surface and become less reactive, so plasma-treated surfaces are best used fresh.

The bond coating systems described herein produce coatings that remain bonded in aqueous fluids on surfaces such as polyethylene, polypropylene, polyamide, polyester, silicone and metals such as stainless steel, platinum, gold, nickel, titanium, nickel-titanium alloys, chrome and other surfaces that are generally considered as presenting adherence problems. It may be necessary to treat some surfaces with gas plasma or other ionizing treatment to promote adhesion to the substrates.

Optionally, one or more tie coat layers may be applied on the bond coat beneath the med coat. A tie coat layer may comprise any suitable material for joining the med coat to the bond coat. Polyurethanes and other materials may be used for this purpose.

Another aspect of the present invention is that a med coat may comprise a hybrid polymeric material comprising hydrophilic and hydrophobic polymers, which are incorporated such that the appropriate degree of hydrophilic/hydrophobic balance is obtained to meet the desired drug release requirements. Polymer matrices that are less hydrophilic will ordinarily have slower moisture diffusion and therefore produce slower drug diffusion rates. More hydrophilic polymer matrices will usually have faster moisture diffusion rates and therefore produce faster drug diffusion rates. Cross-linked polymer matrices will usually have slower diffusion rates than similar polymer matrices that are not cross-linked.

A variety of hydrophilic and hydrophobic polymers for use in such a hybrid are known in the art. For example, suitable hydrophilic polymers include polyvinylpyrrolidone (PVP), PVP/vinyl acetate copolymer (PVP/VA), polyethylene glycol, polyethylene oxide, polyvinyl alcohol, a polyether, polysaccharide, hydrophilic polyurethane, polyhydroxyacrylate, polymethacrylate, dextran, xanthan, hydroxypropyl cellulose, methyl cellulose; or a homopolymer or copolymer of a vinyl compound having polar pendant groups, N-vinyllactam such as N-vinylpyrrolidone, N-vinyl butyrolactam, N-vinyl caprolactam, an acrylate or methacrylate having hydrophilic esterifying groups, hydroxyacrylate, and acrylic acid, polyacrylamide/ethylene glycol copolymer and polyacrylamide/polyethylene oxide copolymer; or a combination thereof. Suitable hydrophobic polymers include a cellulose ester or ether, ethyl cellulose, hydroxyethyl cellulose, cellulose nitrate, cellulose acetate, cellulose acetate butyrate, cellulose acetate propionate, polyurethane, polyacrylates, a natural or synthetic elastomer, rubber that is soluble in organic solvents, acetal, nylon, polyester, styrene polybutadiene, acrylic resin, polyvinylidene chloride, polycarbonate, homo- and copolymers of vinyl compounds, polyvinylchloride, polyvinylchloride acetate, acrylate/carboxyl copolymer and combinations thereof. In a specific embodiment, a hybrid coating may comprise a combination of an acrylate polymer and a PVP/VA copolymer in a weight ratio in the range of from 1.5:1 to 7:1.

The hybrid polymer layer of the devices of the present invention can be formulated to release large amounts of drug at first, followed by a sustained drug release over extended time periods to achieve more efficacious performance. We have now found that surprisingly high drug loads that were not contemplated in prior U.S. Pat. Nos. 5,069,899 and 5,525, 348 can be incorporated in the hybrid polymer layers. These and other prior art patents show coatings impregnated with anti-thrombogenic, anti-microbial and other agents only to the extent to prevent inflammation infection, etc., resulting from the placement of the device in the body ("prophylactic use") and not in amounts that permit the use of the device as a means of delivery of amounts of drugs effective for the therapeutic treatment of such pathologic conditions prior to the introduction of the device ("therapeutic use"). Such elevated loadings can be one, two or even three orders of magnitude greater than is employed in prior art coatings. For example, a device containing prophylactic quantities of a medically active agent, anti-thrombogenic, antibiotic, etc., may contain several micrograms of the agent per square centimeter of the coating surface, whereas a device according to this invention may contain hundreds or thousands of micrograms per square centimeter. The elevated drug loads carried in the hybrid polymer layers therefore make it possible to insert devices that are capable of sustaining greatly elevated medicament(s) burdens, such as anti-cancer drugs in tumors, over extended time periods. The drug release rates can be controlled over wide ranges by several factors, including drug solubility in water and in the patient medium, diffusion rates of body fluids into the hybrid polymer layer, ratio of the drug or drugs to the polymer matrix in the polymer layer, chemical/ physical interactions between the drug or drugs and polymer matrix, the degree of cross-linking in the hybrid polymer layer, the layer thickness of the hybrid polymer base, and the relative proportions of hydrophilic and hydrophobic polymer materials in the coating.

For example, a hybrid polymer coating comprising roughly equal amounts of one or more hydrophilic polymers or copolymers and one or more hydrophobic polymers or copolymers will admit water into the coating at a much greater rate than a coating comprising only a minor proportion of hydrophilic polymers or copolymers. This invention demonstrates that by reducing the proportion of hydrophilic polymers, the coating can be loaded with large amounts of therapeutic agents and that elution will occur over extended periods of time, e.g., at least two weeks, or at least a month or, optionally, several months. Coatings of devices in accordance with this invention can therefore be designed to provide therapeutic amounts of therapeutic agents to tissue in areas of up to one, two or three centimeters from the implant site, whereas prior art devices were typically capable of delivering effective amounts of active agents to areas within only one or two millimeters from the implant site. As demonstrated in the example below, by employing a coating comprising principally hydrophobic polymer materials with a minor proportion of hydrophilic polymer materials, the rate at which a therapeutic agent is delivered to surrounding tissue can be extended and regulated.

Regardless of the relative proportions of hydrophilic and hydrophobic coatings in the coating, higher ratios of drug to polymer binder lead to more rapid drug release rates, while higher ratios of polymer binder to drug(s) result in slower release rates. Drugs which are more soluble in the patient's tissue/fluid medium will release more rapidly from the coating, and less soluble drugs will release more slowly from the coating.

The med coats of this invention are thin (typically less than 200 micrometers (μm) in thickness), and can be smooth or porous. The coats are made to be flexible or rigid, depending on the product mission, but as discussed above, the use of a scaffold or other substrate will alleviate the need to produce a mechanically strong or rigid coating. The hybrid polymer layers may be prepared as generally described in one or more of U.S. Pat. Nos. 5,001,009; 5,069,899; 5,331,027; 5,525,348; 5,800,412; 5,997,517; 6,110,483; PCT/US97/18477; and their U.S. and foreign counterparts. The disclosures of each of the foregoing patents and applications are hereby incorporated herein by reference.

One advantage of this invention is the fact that the layers can accommodate a wide variety of drugs, and the drugs can be incorporated in the same or contiguous layers. The devices and methods of the present invention provide sustained, high efficacious medicament concentrations in selected sites such as tumors or lesions for time periods of from a few days to several weeks. The present invention also provides high medicament concentrations in specific sites, e.g., tumors or lesions, while systemic medicament concentrations are kept to very low, safer levels, much lower than those which are encountered in systemic drug therapy.

One embodiment of a targeted delivery device in accordance with the present invention is illustrated in FIG. 1. The device 10 comprises a carrier substrate 12 and a coating 14 comprising a single medicated polymer layer of polymeric material. Dispersed within the medicated polymer layer is a dose of therapeutic agent schematically represented by dots 16. The polymeric material in coating 14 is chosen for good adherence to carrier substrate 12, which may comprise, e.g., polyvinylchloride (PVC) so that no binder layer is needed between the medicated polymer layer and the substrate. Coating 14 is porous or water-permeable and, upon insertion into tissue, water diffuses into coating 14 as indicated by arrow 18. Therapeutic agent contained within coating 14 is carried by the water out from coating 14 as indicated by arrows 20 and is thus delivered into the adjacent tissue. Therapeutic agent near the exposed surface of coating 14 diffuses out from coating 14 more quickly than therapeutic agent disposed closer to substrate 12. As indicated above, substrate 12 is preferably chosen for its structural properties so that the polymeric material in the medicament-containing layer of coating 14 can be chosen for its diffusion properties rather than its structural properties. Optionally, the medicament-containing layer of coating 14 comprises a hybrid polymer layer of hydrophobic and hydrophilic polymeric materials, as described above. In alternative embodiments, coating 14 may comprise a plurality of layers, optionally a plurality of medicament-containing layers and/or non-medicament-containing layers such as a bond coat layer to enhance adhesion between the other layer (s) and substrate 12.

Devices of the present invention can be used to deliver many kinds of therapeutic agents for therapeutic processes, e.g., anti-cancer agents such as paclitaxel, docetaxel (marketed as TAXOTERE by Aventis Pharmaceuticals Inc.), fluorouracil, doxarubicin, methotrexates, cisplatin, mitomycin, peplomycin, merbarone, alone and in combinations; anti-infective agents including antibiotics such as rifamycin, minocycline, penicillins, cephalosporins, fluoroquinalones, Tetracyclines, Chloramphenicol, Polymixin B sulfate, Bacitracin zinc, aminoglycosides, clindamycin, and lincomycin, and/or anti-microbial agents such as benzalkonium chloride, Bronopol (2-bromo-2-nitropropane-1,3-diol), thymol, silver compounds, benzethonium chloride, stearalkonium chloride, 1,2-benzisothiazolin-3-one, triclosan, and polyhexa-methylene biguanide hydrochloride (a component of VANTOCIL, Arch Chemicals, Inc.), alone and in combinations; anti-thrombogenic agents such as heparin sodium, heparin complexed with quaternary ammonium compounds such as benzalkonium chloride, stearalkonium chloride, or tridodecylmethylammonium chloride, hirudin, sugars, and aspirin, alone and in combinations; anti-viral agents or vector, DNA, enzymes, etc., alone or in combinations. Clotting agents such as thrombin, fibrin, and/or antiangiogenic agents such as Canstatin, paclitaxel, 2C3 anti-vascular endothelial growth factor (from the University of Texas) and peptides are disclosed in U.S. Pat. No. 5,994,309 and may also be incorporated. Any suitable therapeutic agent or combinations of two or more thereof ("drug cocktails") can be delivered by the devices and methods of the present invention.

The following examples are illustrative, and are not intended to limit the scope of the invention.

Example 1

Prior Art Layer on Polyurethane

A quantity of 2 milliliters ("ml") sodium methotrexate (25 mg/ml) was placed in a test tube and 4 ml ethanol was added. The methotrexate precipitated out of solution. Tridodecylmethylammonium chloride (TDMAC) was added in an amount sufficient to react with all the methotrexate present, and the test tube was swirled to mix the agents. The methotrexate quickly went into solution as the TDMA salt. This mixture was shaken with an equal volume of toluene to separate the water and sodium chloride from the methotrexate-TDMA salt. The toluene layer separated to the top and had characteristic yellow color of methotrexate salts. The aqueous layer was clear and had no color. The toluene layer was diluted with an equal volume of 2% cellulose acetate butyrate in butyrolactone. This was coated on a polyurethane catheter surface and produced a clear layer. (This is Example 20, from U.S. Pat. No. 5,525,348, the disclosure of which is incorporated herein by reference.)

Example 2

Prior Art

The following solution was coated on glass and dried for 2 minutes at 80° C.

| | |
|---|---|
| Merbarone | 0.10 gm |
| Dimethyl sulfoxide | 1.98 gm |
| Cellulose acetate butyrate | 0.12 gm |
| Ethanol | 2.0 g, |

This solution was clear, and dried to a clear layer when coated on glass.

Examples 1 and 2 demonstrate that it is possible to formulate homogeneous solutions containing polymer and pharmaceutical agents which can be cast on surfaces and will dry to form clear, homogeneous, polymeric alloy. (This is Example 22 from U.S. Pat. No. 5,525,348, the disclosure of which is incorporated herein by reference.)

Example 3

The following solutions were prepared.

E3-PC

| | |
|---|---|
| Acrylate/carboxyl polymer, 55.5% solution (1) | 8.33 gm |
| Tetrahydrofuran (THF) | 39.58 gm |
| Cyclohexanone | 41.60 gm |
| PVP/VA Polymer Solution (2) | 2.73 gm |
| Ethanol | 1.37 gm |

| | |
|---|---|
| Epoxy polymer Solution (3) | 1.20 gm |

E3 - Med Coat

| | |
|---|---|
| Epoxy Polymer Solution (3) | 2.56 gm |
| PVP/VA Polymer Solution (2) | 2.79 gm |
| Acrylate/carboxyl polymer, 55.5% Solution (1) | 8.50 gm |
| Cyclohexanone | 42.70 gm |
| THF | 36.70 gm |
| Ethanol | 5.56 gm |
| Paclitaxel | 1.00 gm |

(1) This copolymer solution is 55.5% (w/w) solids in aromatic 150/butyl cellosolve, 87.5/12.5.
(2) This copolymer solution is 50/0% (w/w) solids in ethanol.
(3) This epoxy polymer is 75% (w/w) solids in xylene.

Solution E3-PC was coated on stainless steel coronary stents, and dried for 60 minutes at 120° C. This layer was applied twice. Solution E3 —Med Coat was coated over the precoat layers, and dried for 60 minutes at 120° C. Drug loading on the stents in the range of 50-60 μg was achieved by applying the Med Coat three times. The stent samples with three layers of E3—Med Coat were subjected to elution in room temperature phosphate buffered saline for times up to 336 hours, and produced the results set forth in TABLE I.

TABLE I

Test No: A99-155
Test Items: Paclitaxel Extracts

| Sample Identification and Elution Time | Analysis #1 Paclitaxel Conc. (μg/ml) | Analysis #2 Paclitaxel Conc. (μg/ml) | Average Paclitaxel in Eluent (μg/ml) | Extract Volume (ml) |
|---|---|---|---|---|
| TDH042799-1, 2 hr. | 0.6 | 0.7 | 0.65 | 1.5 |
| TDH042799-1, 4 hr. | 0.5 | 0.5 | 0.50 | 1.5 |
| TDH042799-1, 6 hr. | 0.4 | 0.4 | 0.40 | 1.5 |
| TDH042799-1, 8 hr. | 0.3 | 0.4 | 0.35 | 1.5 |
| TDH042799-1, 24 hr. | 0.3 | 0.3 | 0.30 | 1.5 |
| TDH042799-1, 48 hr. | 0.3 | 0.3 | 0.30 | 1.5 |
| TDH042799-1, 168 hr. | 0.4 | 0.4 | 0.40 | 1.5 |
| TDH042799-1, 216 hr. | 0.3 | 0.3 | 0.30 | 1.5 |
| TDH042799-1, 336 hr. | 0.3 | 0.3 | 0.30 | 1.5 |

TABLE II

| Sample Identification | μg Paclitaxel Released | % of Total Paclitaxel released over 336 hours | Elution Time Cumulative Hrs. | Paclitaxel Release Cumulative μg |
|---|---|---|---|---|
| TDH042799-1, 2 hr. | 0.98 | 18.6 | 2 | 0.98 |
| TDH042799-1, 4 hr. | 0.75 | 14.3 | 4 | 1.73 |
| TDH042799-1, 6 hr. | 0.60 | 11.4 | 6 | 2.33 |
| TDH042799-1, 8 hr. | 0.53 | 10.0 | 8 | 2.85 |
| TDH042799-1, 24 hr. | 0.45 | 8.6 | 24 | 3.30 |
| TDH042799-1, 48 hr. | 0.45 | 8.6 | 48 | 3.75 |
| TDH042799-1, 168 hr. | 0.60 | 11.4 | 168 | 4.35 |
| TDH042799-1, 216 hr. | 0.45 | 8.6 | 216 | 4.80 |
| TDH042799-1, 336 hr. | 0.45 | 8.6 | 336 | 5.25 |

Figure 2:
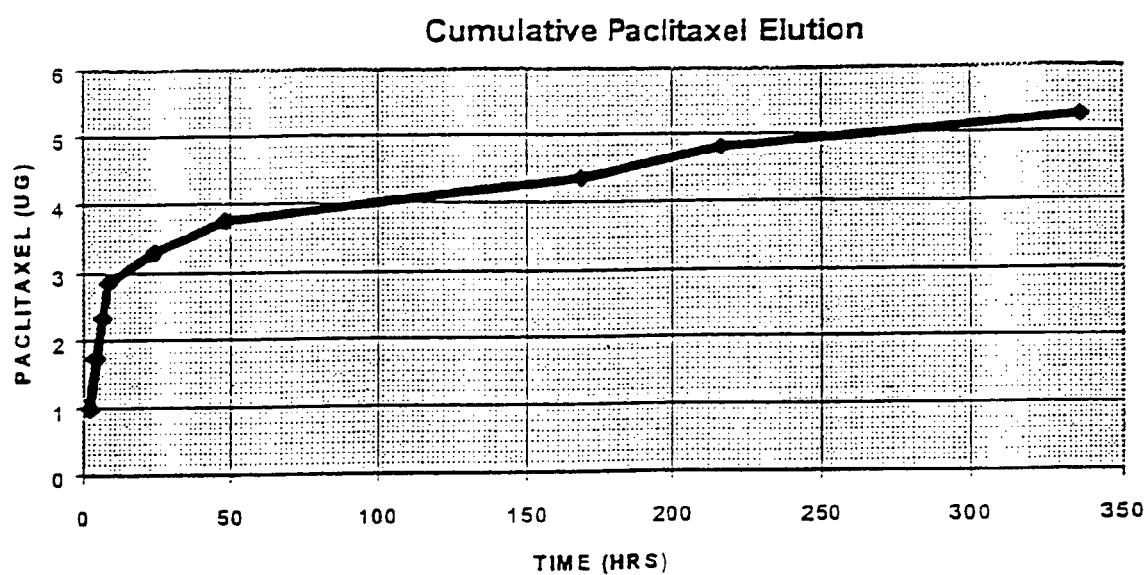
FIG. 2 is a graph plotting the data of Example 3 and showing on the vertical axis the micrograms of a medicament released from a device of the present invention over a period of time plotted on the horizontal axis.

The data of TABLE I and TABLE II show that approximately 10% of the paclitaxel eluted out over a period of 14 days. The data are plotted on the graph of FIG. 2 and show the cumulative quantity of paclitaxel eluted, in micrograms, over a period of 336 hours (14 days).

Example 4

Silicone rubber tubing was dipped briefly in a 4% (w/w) solution of benzoylperoxide, and dried under ambient room conditions. After drying, the tubing was placed in a reactor that contained the following aqueous monomer solution.

| | |
|---|---|
| Acrylamide derivatives | 32.8 gm |
| Diacrylate cross-linker monomer | 2.0 |
| Polyvinylpyrrolidone | 0.16 |
| Sodium Chloride | 120.0 |
| Water to | 800.0 |

The system was degassed at 1.0 mm Hg for ten minutes. The reactor was then placed in a water bath at 87° C. for about one hour, and the reaction system was stirred at low speed on a magnetic stirrer. After the graft reaction, the tubing was rinsed with water and dried. The surface layer displayed excellent adhesion to the silicone tubing when tested with Scotch® tape.

The grafted samples were soaked for five minutes in solutions containing biologically active agents, as shown in the Table below, and rinsed with deionized water and dried. The samples were then tested for elution of active agents by zone of inhibition against staphylococcus A organism. The following table lists the results. It is clear that each of the active agents diffused out of the graft layer over distances of from 6 to 38 mm.

| Physiological Agent | Zone size (mm) against *S. Aureus* (4 samples) |
|---|---|
| 4.8% Rifamycin | 32, 33, 33, 35 |
| 1.9% Gentamicin laurylsulfate | 12, 12, 12, 13 |
| 2.0% VANTOCIL ® IB | 9, 9, 10, 10 |
| 4.8% Benzalkonium chloride | 16, 16, 16, 16 |
| 2.0% BRONOPOL-BOOTS ® BP | 38, 38, 38, 38 |
| 2.1% silvernitrate | 11, 12, 12, 12 |
| 1.0% methotrexate | 10, 11, 11, 11 |
| 1.1% paclitaxel | 6, 6, 6, 7 |

Example 5

Stainless steel coil guide wires of 0.038 inches in diameter (0.965 mm) were sealed in a hybrid polymer sleeve made of polyurethane and cellulose nitrate (PU/CN) polymers. The hybrid polymer is proprietary to STS Biopolymers, Inc. of Henrietta, N.Y. Next, a hybrid polymer layer containing polyvinylpyrrolidone and cellulose nitrate with 33% paclitaxel was cast over the sleeves. The samples were evaluated for drug loading by high pressure liquid chromatography (HPLC) analysis under the following conditions.

Column—10×0.4 cm Hypersil C18, 5 micron
Column temperature—ambient
Mobile phase—1.1 acetonitrile:water
Flow rate—1.0 ml/min
Detector—UV at 228 nm
Injection volume—20 microliters
Retention time—about 6 minutes Results show the following drug loading expressed as micrograms ("μg") of drug per linear centimeter of the wire ("μg/linear cm").

| | |
|---|---|
| Sample 1 | 423 μg/linear cm. |
| Sample 2 | 560 μg/linear cm. |
| Average | 492 μg/linear cm. |

TABLE III

An elution analysis in calf serum was performed with the following results.

| Elution Time | Paclitaxel Remaining |
|---|---|
| 0 days | 408.1 micrograms/centimeter |
| 1 day | 298.0 micrograms/centimeter |
| 3 days | 132.4 micrograms/centimeter |
| 5 days | 68.3 micrograms/centimeter |
| 7 days | 29.2 micrograms/centimeter |

Example 6

Three coating formulations designated A, B and C were prepared as follows.

TABLE IV (All percents are expressed as w/w %.)

| Component | A | B | C |
|---|---|---|---|
| Benzalkonium heparinate (HBAK) | 2.00% | 2.00% | 2.00% |
| Hydrophobic polyurethane | 4.30% | 0.00% | 0.00% |
| Ultra Hydrophilic polyurethane | 0.00% | 4.30% | 0.00% |
| Hydrophobic polyurethane | 0.00% | 0.00% | 3.65% |
| Nitrocellulose, RS, 5-6 sec. | 4.30% | 4.30% | 4.30% |
| Polyvinylpyrrolidone (PVP) | 0.00% | 0.00% | 0.65% |
| N-methylpyrrolidone | 16.40% | 16.40% | 16.40% |
| Tetrahydrofuran | 25.90% | 25.90% | 25.90% |
| Ethanol | 47.10% | 47.10% | 47.10% |

Each of the coatings was applied to a tube substrate to approximate the loading on a stent and the resulting devices were tested for drug release by placing them in serum and incubating them at 37° C. with continuous gentle swirling. The serum was exchanged with fresh serum every Monday, Wednesday and Friday. The results, indicating the heparin content of the serum measured on the indicated day are set forth in TABLE V.

TABLE V (Data indicate estimated USP heparin units released into the serum per cm of the substrate.)

| | Device Coating | | |
|---|---|---|---|
| Day | A | B | C |
| 1 | 0.275 | 1.58 | 0.68 |
| 2 | 0.275 | 1.75 | 0.65 |
| 4 | 0.02 | 1.8 | 0.4 |
| 7 | 0.02 | 0.9 | 0.55 |
| 11 | 0.02 | 0.7 | 0.38 |
| 14 | 0.02 | 0.8 | 0.35 |
| 18 | 0.02 | 0.5 | 0.13 |
| 21 | 0.02 | 0.5 | 0.1 |
| 25 | 0.01 | 0.5 | 0.08 |

These data show that samples C provided a longer and more uniform release of the drug than did either of the other two samples. Sample C differed from Samples A and B in that Sample C contained principally hydrophobic polymer materials with a small amount of a hydrophilic material (PVP). In contrast, Sample A contained only hydrophobic polymer materials and Sample B contained approximately equal quantities of hydrophobic and hydrophilic materials. The data therefore show that by employing a minor proportion of hydrophilic material in a hybrid polymer coating, the release of a therapeutic agent can be well regulated.

Example 7

Three coating materials designated E, F and G were prepared as follows.

TABLE VI

| Component | E | F | G |
|---|---|---|---|
| Hydrophilic polyurethane | 6.07% | 0.00% | 1.50% |
| Ultra hydrophilic polyurethane | 0.00% | 6.07% | 0.00% |
| Hydrophobic polyurethane | 0.00% | 0.00% | 1.50% |
| Nitrocellulose RS, 5-6 sec. | 2.43% | 2.43% | 1.20% |
| Tetrahydrofuran | 54.64% | 54.64% | 51.30% |
| Ethanol | 21.85% | 21.85% | 20.60% |
| Dimethyl-sulfoxide | 15.01% | 15.01% | 23.90% |

Two portions of coating material E and two portions of coating material G, designated E1, E2, G1 and G2, respectively, were prepared. E1 and G1 each contained 6% paclitaxel while E2 and G2 each contained 6% paclitaxel and 2% HBAK. The coatings were then coated onto wire substrates to simulate stents and the resulting devices were tested as described in Example 6. The results at the start, and on days 1, 3 and 7 are set forth in the following TABLE VII.

TABLE VII

| | Days | | | |
|---|---|---|---|---|
| Device Coating | 0 | 1 | 3 | 7 |
| E1 | 140 | 71 | 45 | 18 |
| E2 | 122 | 49 | 32 | — |
| G1 | 119 | 48 | 30 | — |
| G2 | 102 | 45 | 22 | — |

(Data indicate μg paclitaxel released from the simulated stent at the indicated day.)

The data of TABLE VII show that the combination of an anti-thrombogenic agent with an anticancer agent in the polymer coating does not substantially affect the elution rate of the anticancer agent.

A 6% quantity of paclitaxel was added to coating material F and several substrates were then coated with material F. The resulting devices were tested as described above and measurements were made by stripping the substrates at the start, and on days 1, 3, 7, 10, 14, 21 and 28 to determine the paclitaxel loading on the substrate. The results are set forth in TABLE VIII as follows (each datum being the average measurement from two samples taken on the indicated day).

TABLE VIII

| Day | 0 | 1 | 3 | 7 | 10 | 14 | 21 | 28 |
|---|---|---|---|---|---|---|---|---|
| μg paclitaxel | 770 | 840 | 460 | 230 | 490 | 18 | 17 | 20 |

(Data indicate the amount of paclitaxel remaining in the coating on the indicated day.)

Allowing for minor variations in the original paclitaxel content among the samples, the data for TABLE VIII show that therapeutic quantities of paclitaxel are available in the coating even after 28 days of elution.

While the invention has been described with reference to specific embodiments thereof, it will be apparent upon a reading and understanding of the foregoing that numerous alterations to the described embodiments will occur to those of ordinary skill in the art and it is intended to include such alterations within the scope of the appended claims.

What is claimed is:

1. A medicated device comprising:
   a substrate comprising adjacent edges or surfaces in close proximity to each other defining an opening; and
   a coating bridging from one edge or surface to another across the opening, and said coating comprising at least one polymer and at least one therapeutic agent,
   said therapeutic agent being at a loading of at least about 100 micrograms per square centimeter of coating.

2. The medicated device of claim 1, said therapeutic agent being at a loading of at least about 500 micrograms per square centimeter of coating.

3. The medicated device of claim 1, said substrate having a shape selected from the group consisting of mandrels, beads, egg-shapes, spheres, and threads.

4. The medicated device of claim 1, said therapeutic agent being an antiangiogenic agent.

5. The medicated device of claim 1, said therapeutic agent being an antiviral agent.

6. The medicated device of claim 1, said therapeutic agent being one or more selected from the group consisting of docetaxel, doxarubicin, mitomycin, peplomycin, minocycline, penicillins, cephalosporins, fluoroquinalones, tetracyclines, Chloramphenicol, Polymixin B sulfate, Bacitracin zinc, clindamycin, lincomycin, 1,2-benzisothiazolin-3-one, triclosan, polyhexa-methylene biguanide hydrochloride, hirudin, and aspirin.

7. The medicated device of claim 1, said therapeutic agent being one or more selected from the group consisting of polyhexa-methylene biguanide hydrochloride and 2-bromo-2-nitropropane-1,3-diol.

8. The medicated device of claim 1, said therapeutic agent comprising paclitaxel.

9. A method for making a medicated device, comprising the steps of:
   providing a substrate comprising edges or surfaces in close proximity to each other defining an opening;
   providing a coating material comprising at least one polymer and at least one therapeutic agent; and,
   applying the coating material to said substrate to produce a coating bridging from one edge or surface to another across the opening, the therapeutic agent being at a loading of at least about 5 micrograms per square centimeter of coating material.

10. The method of claim 9, comprising applying a polymeric coating sheath to said substrate, and applying to said sheath a layer of said coating material.

11. The method of claim 9, wherein said therapeutic agent is in the coating at a loading of at least about 100 micrograms per square centimeter of coating.

12. A method of providing a therapeutic agent to a target tissue, comprising the steps of:
   providing a medicated device comprising a substrate comprising adjacent edges or surfaces in close proximity to each other defining an opening, a coating bridging from one edge or surface to another across the opening, and said coating containing at least one polymer and at least one therapeutic agent and comprising one or more layers; and,
   inserting the medicated device into the target tissue to provide therapeutic benefit, wherein a therapeutic amount of said therapeutic agent diffuses into the tissue at least about one centimeter from said device.

13. The method of claim 12, wherein said therapeutic agent is at a loading of at least about 100 micrograms per square centimeter of coating.

14. The method of claim 12, the tissue comprising a tumor or a lesion.

15. The method of claim 12, said inserting comprising inserting the medicated device into a tumor, wherein said therapeutic agent comprises an anti-cancer drug.

16. The method of claim 12, said inserting comprising inserting the medicated device into a lesion, wherein said therapeutic agent comprises an antibiotic.

17. The method of claim 12, further comprising inserting the medicated device using a trochar or catheter.

18. A medicated device comprising:
a substrate suitable for implantation into a patient's body and comprising adjacent edges or surfaces in close proximity to each other defining an opening; and
a formulation comprising at least one polymer and at least one therapeutic agent, the formulation bridging from one edge or surface to another across the opening, the therapeutic agent being at a loading sufficient to deliver a therapeutically effective quantity of the therapeutic agent when implanted in the patient's body.

19. The device of claim 18 wherein the substrate has an open, perforated, or mesh structure providing support for the formulation.

20. The device of claim 18 wherein the substrate is a stent.

21. The device of claim 18 wherein the therapeutic agent comprises paclitaxel.

22. The device of claim 18 wherein the substrate is a stent and the therapeutic agent comprises paclitaxel.

23. The device of claim 22 wherein the stent elutes about 10% of the paclitaxel over about 14 days.

24. The medicated device of claim 18, wherein said therapeutic agent is at a loading of at least about 100 micrograms per square centimeter of the coating.

25. A medicated device comprising:
a substrate comprising adjacent edges or surfaces in close proximity to each other defining an opening; and
a coating bridging from one edge or surface of the substrate to another across the opening, and said coating comprising at least one polymer and at least one therapeutic agent at a loading sufficient to deliver a therapeutically effective quantity of the therapeutic agent when implanted in a patient's body.

26. The medicated device of claim 25, said coating comprising a bond coat layer and a layer comprising the therapeutic agent.

27. The medicated device of claim 25, said substrate comprising a wire configured into a coil.

28. The medicated device of claim 27, said coil having open windings.

29. The medicated device of claim 25, said substrate selected from the group consisting of perforated wafers and wire meshes.

30. The medicated device of claim 25, said substrate selected from the group consisting of mandrels, beads, cylinders, egg-shaped articles, spheres, coiled articles, straight articles, threads, wires, pellets, tubing, and stents.

31. The medicated device of claim 25, wherein when said device is implanted in a tissue, a therapeutic amount of said therapeutic agent diffuses at least about one centimeter from said device.

32. The medicated device of claim 25, wherein in a zone of inhibition test, effective amounts of the therapeutic agent diffuse at least about one half centimeter from said device.

33. The medicated device of claim 25, said therapeutic agent being one or more selected from the group consisting of an antibiotic agent, an anticancer agent, an antiangiogenic agent, an antimicrobial agent, an antiviral agent, and an antithrombogenic agent.

34. The medicated device of claim 25, said therapeutic agent being one or more selected from the group consisting of docetaxel, fluorouracil, doxarubicin, cisplatin, mitomycin, peplomycin, merbarone, minocycline, penicillins, cephalosporins, fluoroquinalones, tetracyclines, Chloramphenicol, Polymixin B sulfate, Bacitracin zinc, aminoglycosides, clindamycin, lincomycin, thymol, silver compounds, benzethonium chloride, stearalkonium chloride, 1,2-benzisothiazolin-3-one, triclosan, polyhexa-methylene biguanide hydrochloride, heparin sodium, heparin complexed with a quaternary ammonium compound, heparin complexed with benzalkonium chloride, heparin complexed with stearalkonium chloride, heparin complexed with tridodecylmethylammonium chloride, hirudin, sugars, and aspirin.

35. The medicated device of claim 25, said therapeutic agent being one or more selected from the group consisting of rifamycin, gentamicin laurylsulfate, polyhexa-methylene biguanide hydrochloride, benzalkonium chloride, 2-bromo-2-nitropropane-1,3-diol, silver nitrate, and methotrexate.

36. The medicated device of claim 25, said therapeutic agent comprising heparin and at least one additional agent.

37. The medicated device of claim 25, said coating comprising at least one hydrophobic polymer and at least one hydrophilic polymer.

38. The medicated device of claim 25, said coating comprising a first polymer and a second polymer, said first polymer being more hydrophilic than said second polymer.

39. The medicated device of claim 37, said hydrophilic polymer comprising a polymer being one or more selected from the group consisting of a polyacrylamide/ethylene glycol copolymer, a polyacrylamide/polyethylene oxide copolymer, polyvinylpyrrolidone, polyvinylpyrrolidone vinylacetate copolymer, a polyethylene glycol, and a polyethylene oxide.

40. The medicated device of claim 37, said hydrophobic polymer comprising an acrylate/carboxyl copolymer, a cellulose ester polymer, cellulose nitrate, a polyurethane polymer, an acrylate polymer, and an acrylate copolymer.

41. The medicated device of claim 37, said coating comprising at least as much hydrophobic polymer as hydrophilic polymer by weight.

42. The medicated device of claim 37, said coating comprising hydrophobic polymer and hydrophilic polymer in a weight ratio in the range of from about 1.5:1 to about 7:1.

43. The medicated device of claim 25, said coating comprising an acrylate polymer and polyvinylpyrrolidone/vinyl acetate copolymer in a weight ratio in the range of from about 1.5:1 to about 7:1.

44. The medicated device of claim 25, wherein the therapeutic agent comprises an antithrombogenic and/or an antiangiogenic agent in an effective amount.

45. The medicated device of claim 25, wherein said coating comprises at least one antithrombogenic agent.

46. The medicated device of claim 25, wherein said coating comprises at least one antiangiogenic agent.

47. The medicated device of claim 25, wherein said substrate comprises metal.

48. The medicated device of claim 25, wherein said coating comprises paclitaxel.

49. The medicated device of claim 47, wherein said substrate is a stent.

50. The medicated device of claim 25, said therapeutic agent comprising paclitaxel.

51. The medicated device of claim 25, said therapeutic agent selected from the group consisting of heparin sodium and heparin complexed with a quaternary ammonium compound.

52. The medicated device of claim 25, wherein the at least one polymer comprises a poly(L-lactic acid) blend.

53. The medicated device of claim 25, wherein the at least one polymer comprises a polyester.

54. A medicated device, comprising:
   a therapeutic agent;
   means for containing the therapeutic agent; and
   means for providing structural support to the containing means, wherein the containing means bridges from one portion of the structural support providing means to another portion of the structural support providing means, wherein the therapeutic agent is at a loading sufficient to deliver a therapeutically effective quantity of the therapeutic agent in a patient's body when the device is implanted therein.

55. The medicated device of claim 54, wherein the structural support providing means is selected from the group consisting of a perforated wafer, a wire mesh, and a stent.

56. The medicated device of claim 54, wherein the therapeutic agent comprises paclitaxel.

57. The medicated device of claim 54, the therapeutic agent being at a loading of at least about 5 micrograms per square centimeter of the containing means.

58. The medicated device of claim 54, the therapeutic agent being at a loading of at least about 50 micrograms per square centimeter of the containing means.

59. The medicated device of claim 54, the therapeutic agent being at a loading of at least about 100 micrograms per square centimeter of the containing means.

60. The medicated device of claim 54, the therapeutic agent being at a loading of at least about 500 micrograms per square centimeter of the containing means.

* * * * *